US010449435B2

(12) United States Patent
Kim

(10) Patent No.: US 10,449,435 B2
(45) Date of Patent: Oct. 22, 2019

(54) SYSTEM FOR PROVIDING A VIRTUAL EXERCISE PLACE

(71) Applicant: Jae Hwan Kim, Jeollanam-do (KR)

(72) Inventor: Jae Hwan Kim, Jeollanam-do (KR)

(*) Notice: Subject to any disclaimer, the term of this patent is extended or adjusted under 35 U.S.C. 154(b) by 0 days.

(21) Appl. No.: 16/101,712

(22) Filed: Aug. 13, 2018

(65) Prior Publication Data

US 2019/0143193 A1 May 16, 2019

(30) Foreign Application Priority Data

Nov. 15, 2017 (KR) ........................ 10-2017-0152555

(51) Int. Cl.
*A63B 71/06* (2006.01)
*G16H 20/30* (2018.01)
*A63B 24/00* (2006.01)

(52) U.S. Cl.
CPC ......... *A63B 71/0622* (2013.01); *G16H 20/30* (2018.01); *A63B 24/0084* (2013.01); *A63B 2024/009* (2013.01); *A63B 2071/0644* (2013.01)

(58) Field of Classification Search
CPC .... A63B 2024/0065; A63B 2024/0068; A63B 2024/0071; A63B 2024/0078; A63B 2024/0081; A63B 2024/009; A63B 2024/0093; A63B 2024/0096; A63B 2071/0625; A63B 2071/0627; A63B 2071/063; A63B 2071/0633; A63B 2071/0636; A63B 2071/0638;

(Continued)

(56) References Cited

U.S. PATENT DOCUMENTS 7,497,812 B2 * 3/2009 Neff ...................... A63B 21/008
482/51
7,833,135 B2 * 11/2010 Radow ............... A63B 22/0605
482/4

(Continued)

FOREIGN PATENT DOCUMENTS

KR   1020050021032 A   3/2005
KR   1020070115210 A   12/2007

(Continued)

OTHER PUBLICATIONS

Korean Patent Application No. 10-2017-0152555, Grant of Patent dated Mar. 27, 2018, 2 pages.

(Continued)

*Primary Examiner* — Garrett K Atkinson
(74) *Attorney, Agent, or Firm* — Lathrop Gage LLP

(57) ABSTRACT

Some implementations of the disclosed technology relate to a system for providing a virtual exercise place, comprising: an image information database in which location-based image data related to a virtual exercise place is stored; and an image data controller selecting from the image information database location-based image data related to a virtual exercise place received from the terminal and providing the selected location-based image data to the terminal, displaying in the terminal an image corresponding to an exercise start location received from the terminal, receiving exercise distance information calculated by the fitness equipment, and displaying in the terminal an image corresponding to a location moved by the exercise distance from the exercise start location.

5 Claims, 7 Drawing Sheets

(58) Field of Classification Search
CPC .... A63B 2071/0641; A63B 2071/0644; A63B 24/00; A63B 24/0062; A63B 24/0075; A63B 24/0084; A63B 24/0087; A63B 71/00; A63B 71/06; A63B 71/0619; A63B 71/0622; G06F 19/30; G06F 19/32; G06F 19/321; G06F 19/324; G06F 19/325; G06F 19/328; G06F 19/34; G06F 19/3418; G06F 19/3481; G06Q 50/22; G06Q 50/24; G16H 20/00; G16H 20/30
See application file for complete search history.

(56) References Cited

U.S. PATENT DOCUMENTS

| | | | | |
|---|---|---|---|---|
| 8,103,517 B2 * | 1/2012 | Hinnebusch | ......... | G09B 19/003 705/1.1 |
| 2002/0055419 A1 * | 5/2002 | Hinnebusch | ......... | G09B 19/003 482/8 |
| 2007/0093360 A1 * | 4/2007 | Neff | ..................... | A63B 21/008 482/8 |
| 2009/0011907 A1 * | 1/2009 | Radow | ............... | A63B 24/0084 482/57 |
| 2014/0046677 A1 * | 2/2014 | Bar-Or | ................ | G06F 19/3475 705/2 |
| 2015/0302766 A1 * | 10/2015 | Oberlander | ............ | G06Q 10/10 434/247 |

FOREIGN PATENT DOCUMENTS

| | | |
|---|---|---|
| KR | 100853993 B1 | 8/2008 |
| KR | 1020090129077 A | 12/2009 |
| KR | 1020100113945 A | 10/2010 |
| KR | 101461202 B1 | 11/2014 |
| KR | 101874262 B1 | 7/2018 |

OTHER PUBLICATIONS

Korean Patent Application No. 10-2017-0152555, Office Action dated Dec. 12, 2017, 12 pages.
Korean Patent Application No. 10-2017-0152555, Certificate of Patent, 1 page.

* cited by examiner

SYSTEM FOR PROVIDING A VIRTUAL EXERCISE PLACE

CROSS-REFERENCE TO RELATED APPLICATION

This application claims priority to and the benefit of Korean Patent Application No. 10-2017-0152555 filed on Nov. 15, 2017. The above application is all hereby incorporated by reference for all purposes as if fully set forth herein.

TECHNICAL FIELD

Some implementations of the disclosed technology relate to a system for providing a virtual exercise place, wherein the virtual exercise place selected by a user is displayed and the user can take exercise while sharing the display of the selected virtual exercise place with another user.

BACKGROUND

The importance of exercise cannot be emphasized enough. However, the problem is that exercise cannot continue for a long period because it is boring and difficult. In particular, exercise alone, for example, walking, running or cycling is exercise that a user alone has to achieve a target amount without a partner. A user requires a strong will in order to continue exercise for a long period. In general, in the case of exercise alone, a user brightens up dull moments while watching a movie or broadcast program from a monitor positioned on the front of fitness equipment. However, it is difficult to find out a movie or broadcast program suitable for an exercise time every time. As a result, this makes it difficult to maintain an interest in exercise for a long period.

Exercise alone may continue for a long period when it is taken along with a partner. To this end, a user may use treadmills or cycling equipment positioned in parallel along with a partner. In this case, the number of partners with whom a user can talk and exercise are not more than two persons left and right. In particular, partners must arrive at an exercise place on an agreed time and place and pieces of not-occupied fitness equipment positioned in parallel must be secured. As a result, not losing an interest in exercise for a long period is limited.

SUMMARY

Various implementations are provided to introduce a unique manner of providing a virtual exercise place, wherein a virtual exercise place selected by a user is displayed on a screen around fitness equipment and the user can take exercise along with another user while sharing the display of the selected virtual exercise place with another user in real time so that the user can take exercise while virtually moving within the selected virtual exercise place.

Some implementations of the disclosed technology provide a system for providing a virtual exercise place, which is connected to a terminal and fitness equipment capable of calculating an exercise distance and transmits an image of a virtual exercise place to the terminal. In some implementations, the system comprises: an image information database in which location-based image data related to a virtual exercise place is stored; and an image data controller selecting from the image information database location-based image data related to a virtual exercise place received from the terminal and providing the selected location-based image data to the terminal, displaying in the terminal an image corresponding to an exercise start location received from the terminal, receiving exercise distance information calculated by the fitness equipment, and displaying in the terminal an image corresponding to a location moved by the exercise distance from the exercise start location (hereinafter referred to as a "virtual current location").

In one aspect, when the virtual current location reaches a course selection point of the location-based image data, the image data controller transmits a course selection message to the terminal and displays in the terminal an image corresponding to a course selected from the terminal.

In another aspect, the image information database comprises gradient data of each location of the location-based image data, and the system further comprises a slope activation unit connected to a load control device of the fitness equipment and applying to the fitness equipment a load based on gradient data corresponding to the virtual current location.

Some implementations of the disclosed technology provide a system for providing a virtual exercise place, which is connected to terminals and fitness equipment capable of calculating exercise distances and transmits an image of a virtual exercise place to the terminals. In some implementations, the system comprises: an image information database in which location-based image data related to a virtual exercise place is stored; a participant setting unit transmitting to a second terminal a signal asking an exercise participation intention received from a first terminal and receiving an exercise participation approval signal from the second terminal; and an image data controller selecting from the image information database location-based image data related to a virtual exercise place received from the first terminal and transmitting the selected location-based image data to the first terminal and the second terminal, displaying in the first terminal and the second terminal an image corresponding to an exercise start location received from the first terminal or the second terminal, receiving exercise distance information calculated by first fitness equipment and second fitness equipment, and displaying in the first terminal and the second terminal an image corresponding to a location moved by the exercise distance from the exercise start location (hereinafter referred to as a "virtual current location").

In one aspect, when the virtual current location reaches a course selection point of the location-based image data, the image data controller transmits a course selection message to the first terminal and the second terminal and displays in the first terminal and the second terminal an image corresponding to a course first selected by any one of the first terminal and the second terminal.

In another aspect, each of the first terminal and the second terminal comprises a camera and a microphone, and the system further comprises a video chatting controller receiving from the first terminal and the second terminal video data of a first user using the first terminal and a second user using the second terminal, photographed by the cameras of the first terminal and the second terminal, and audio data comprising voices of the first user and the second user, recorded by the microphones of the first terminal and the second terminal, transmitting the video data and audio data of the first user to the second terminal, and transmitting the video data and audio data of the second user to the first terminal.

In another aspect, the image information database comprises gradient data of each location of the location-based image data, and the system further comprises a slope activation unit connected to load control devices of the first fitness equipment and the second fitness equipment and applying to the first fitness equipment and the second fitness equipment a load based on gradient data corresponding to the virtual current location.

According to the implementations of the disclosed technology, a mechanism is provided to display a virtual exercise place selected by a user on a screen around fitness equipment, enable a user to take exercise while virtually moving within the selected virtual exercise place, and enable the user to take exercise while sharing the display of the selected virtual exercise place with another user whom the user meets in the virtual exercise space.

Some implementations of the disclosed technology provide a system for providing a virtual exercise place, which is connected to terminals comprising a camera and a microphone and fitness equipment capable of calculating exercise distances and transmits an image of a virtual exercise place to the terminals. In some implementations, the system comprises: an image information database in which location-based image data related to a virtual exercise place is stored; a participant setting unit transmitting to a second terminal a signal asking an exercise participation intention received from a first terminal and receiving an exercise participation approval signal from the second terminal; an image data controller selecting from the image information database location-based image data related to a virtual exercise place received from the first terminal and transmitting the selected location-based image data to the first terminal and the second terminal, displaying in the first terminal and the second terminal an image corresponding to an exercise start location received from the first terminal or the second terminal, receiving exercise distance information calculated by first fitness equipment and second fitness equipment, and displaying in the first terminal and the second terminal an image corresponding to a location moved by the exercise distance from the exercise start location (hereinafter referred to as a "virtual current location"); and a video chatting controller receiving from the first terminal and the second terminal video data of a first user using the first terminal and a second user using the second terminal, photographed by the cameras of the first terminal and the second terminal, and audio data comprising voices of the first user and the second user, recorded by the microphones of the first terminal and the second terminal, transmitting the video data and audio data of the first user to the second terminal, and transmitting the video data and audio data of the second user to the first terminal, wherein when a virtual current location of a third terminal to which the first terminal did not transmit a signal asking an exercise participation intention is close to the virtual current location of the first terminal or the second terminal, the video chatting controller receives from the third terminal video data of a third user using the third terminal, photographed by the camera of the third terminal, and audio data comprising voices of the third user, recorded by the microphone of the third terminal, transmits the video data and audio data of the third user to the first terminal and the second terminal, and transmits the video data and audio data of the first user and the second user to the third terminal, and wherein when the third terminal transmits a joint signal to the first terminal or the second terminal through the participant setting unit, the video chatting controller displays in the third terminal an image corresponding to the virtual current location of the first terminal and the second terminal.

BRIEF DESCRIPTION OF DRAWINGS

A brief description of each drawing is provided so that the drawings cited in this specification are understood more fully.

DETAILED DESCRIPTION

Figure 1:
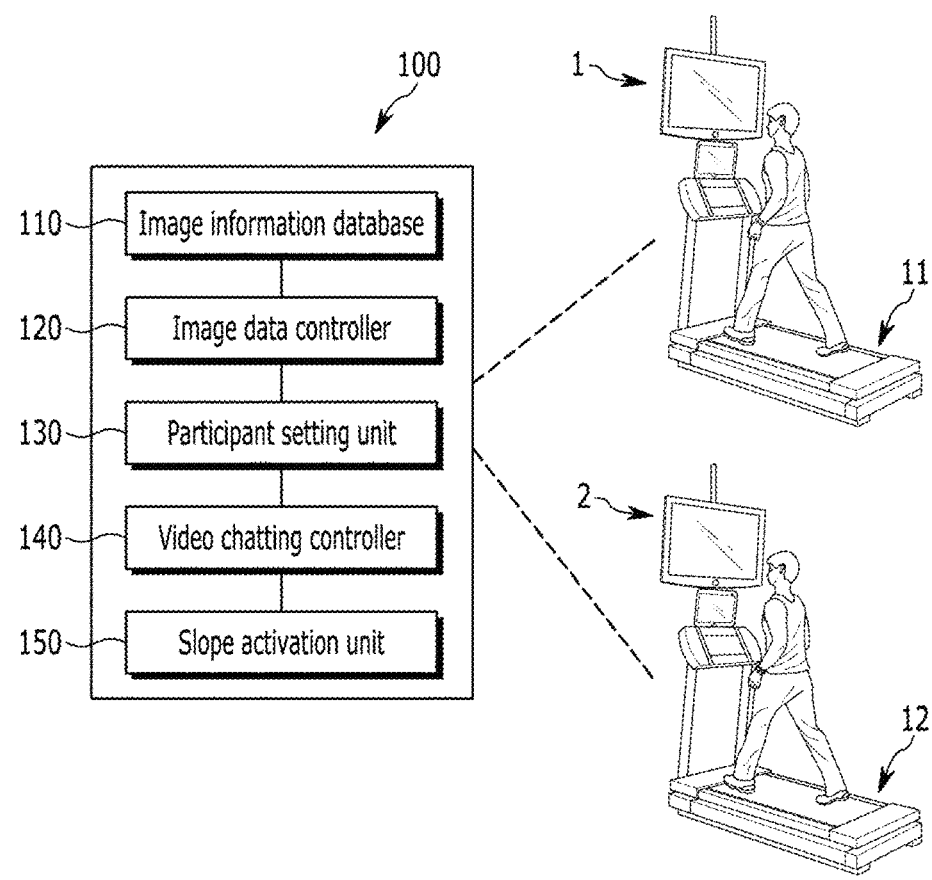
FIG. 1 is an exemplary diagram showing a schematic configuration of a system for providing a virtual exercise place according to an implementation of the disclosed technology.

Some implementations of the disclosed technology are illustrated in the drawings and are described in detail through the detailed description. It is however to be understood that the disclosed technology is not intended to be limited to the specific implementations and the disclosed technology includes all changes, equivalents and substitutions which fall within the spirit and technological scope of the disclosed technology.

Hereinafter, various implementations of the disclosed technology will be described in detail with reference to the accompanying drawings so that those skilled in the art can easily carry out the disclosed technology. In the following detailed description of the embodiments of the disclosed technology, a detailed description of known functions or configurations will be omitted. The same reference numerals are used throughout the drawings for portions having similar functions and actions. Furthermore, numbers (for example, the first and the second) used in the entire specification are merely identification symbols for distinguishing one element from the other element.

In addition, in the entire specification, when a part is referred to as being "connected" with another part, it is not only a case where it is directly connected, but also a case where it is indirectly connected with another element therebetween. Also, "comprising" and "including" mean that other components may be included, rather than excluding other components, unless specifically stated otherwise.

The term "unit" as used herein may include software, hardware, or a combination thereof depending on the context in which the term is used. For example, the software may be machine code, firmware, embedded code, application software, or a combination thereof. Also, for example, the hardware may be a circuit, a processor, a computer, an integrated circuit, integrated circuit cores, or a combination thereof. Two or more elements expressed as "unit" may be merged into a single element or one element may be divided into two or more elements for each subdivided function.

Hereinafter, various implementations of the disclosed technology will be described in detail with reference to the accompanying drawings so that those skilled in the art can easily carry out the disclosed technology.

Figure 2:
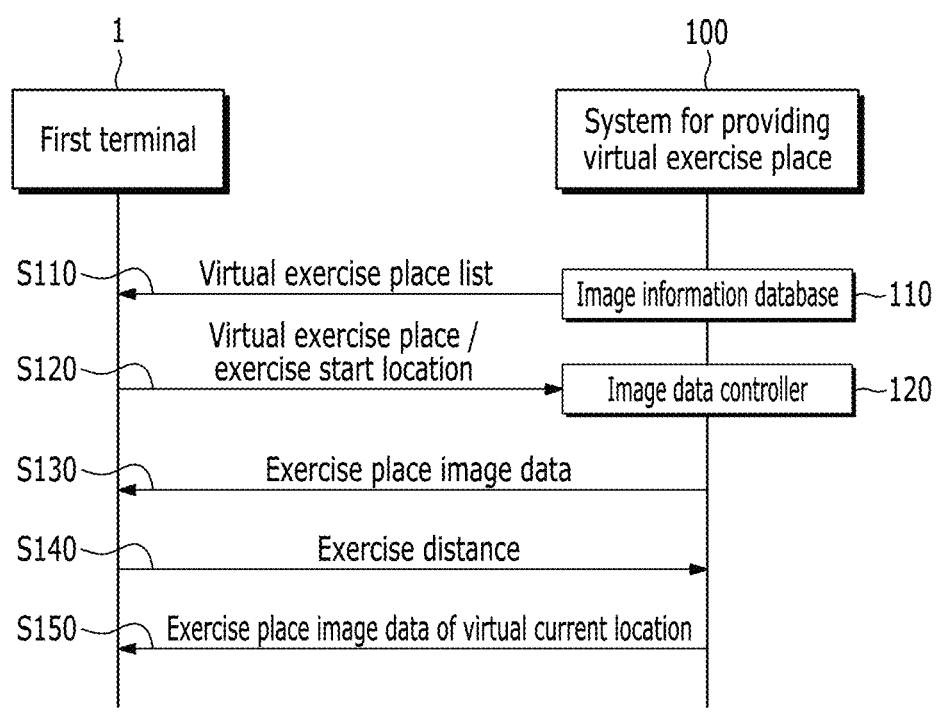
FIG. 2 is an exemplary flowchart showing a method of providing a virtual exercise place in the system for providing a virtual exercise place according to an implementation of the disclosed technology.

FIG. 1 is an exemplary diagram showing a schematic configuration of a system for providing a virtual exercise place according to an implementation of the disclosed technology. FIG. 2 is an exemplary flowchart showing a method of providing a virtual exercise place in the system for providing a virtual exercise place according to an implementation of the disclosed technology.

The system 100 for providing a virtual exercise place according to an embodiment of the disclosed technology may be connected to at least one terminal 1 and 2, and at least one piece of fitness equipment 11 and 12 capable of calculating an exercise distance over a network and perform a function of transmitting an image of a virtual exercise place to the terminal.

In this case, the network means connection architecture through which information can be exchanged between nodes, such as terminals, fitness equipment and servers. Examples of the network include a 3$^{rd}$ Generation Partnership Project (3GPP) network, a Long Term Evolution (LTE) network, a World Interoperability for Microwave Access (WIMAX) network, the Internet, a Local Area Network (LAN), a Wireless Local Area Network (Wireless LAN), a Wide Area Network (WAN), a Personal Area Network (PAN), a Bluetooth network, a satellite broadcasting network, an analog broadcasting network, and a Digital Multimedia Broadcasting (DMB) network, but are not limited thereto.

The terminal of a user may be implemented using a computer capable of accessing a server or terminal at a remote place over the network. In this case, the computer may include a notebook, desktop, laptop, etc. on which a web browser has been mounted, for example. Furthermore, the terminal of a user may be implemented using a terminal capable of accessing a server or terminal at a remote place over the network. The terminal of a user is a wireless communication device that guarantees portability and mobility, for example. The terminal may include all of kinds of handheld-based wireless communication devices, such as a Personal Communication System (PCS), a Global System for Mobile communications (GSM), Personal Digital Cellular (PDC), a Personal Handyphone System (PHS), a Personal Digital Assistant (PDA), International Mobile Telecommunication (IMT)-2000, Code Division Multiple Access (CDMA)-2000, W-Code Division Multiple Access (W-CDMA) and Wireless Broadband Internet (Wibro) terminals, a smartphone, a smartpad, and a tablet PC. The terminals 1 and 2 are installed on the front, side or upper part of the fitness equipment 11 and 12 and preferably include large-sized monitors capable of displaying an image. Furthermore, the terminal preferably includes a camera and a microphone. The fitness equipment is fitness equipment, such as a treadmill or cycling equipment. Equipment using a method of calculating a moving distance based on exercise may be applied to the fitness equipment.

The system 100 for providing a virtual exercise place may include an image information database 110, an image data controller 120, a participant setting unit 130, a video chatting controller 140 and a slope activation unit 150.

The image information database 110 is a data storage server and may store location-based image data related to a virtual exercise place. For example, the image information database may store image data captured by a 360-degree camera every coordinate value based on GPS coordinates. Any place in the world may become a virtual exercise place. Furthermore, the image information database 110 may include gradient data corresponding to each location of location-based image data related to a virtual exercise place. For example, the image information database may store gradient data including a measured slope for all the directions of 360 degrees based on GPS coordinates.

Figure 3:
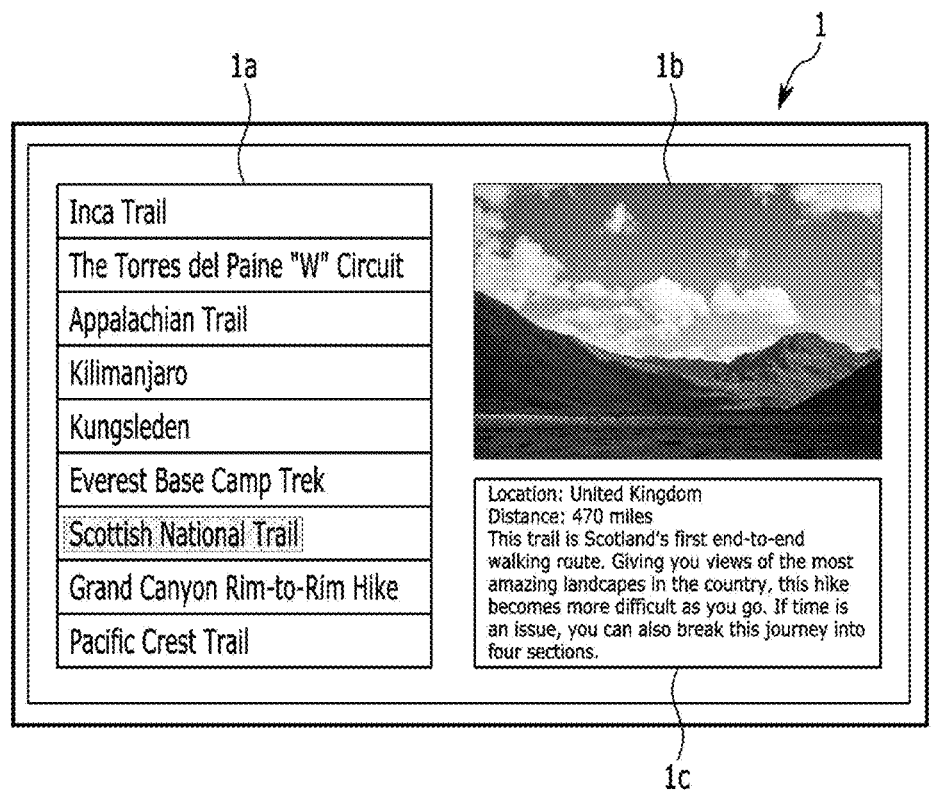
FIG. 3 is an exemplary diagram showing a virtual exercise place selection screen displayed in a terminal of the system for providing a virtual exercise place according to an implementation of the disclosed technology.
Figure 4:
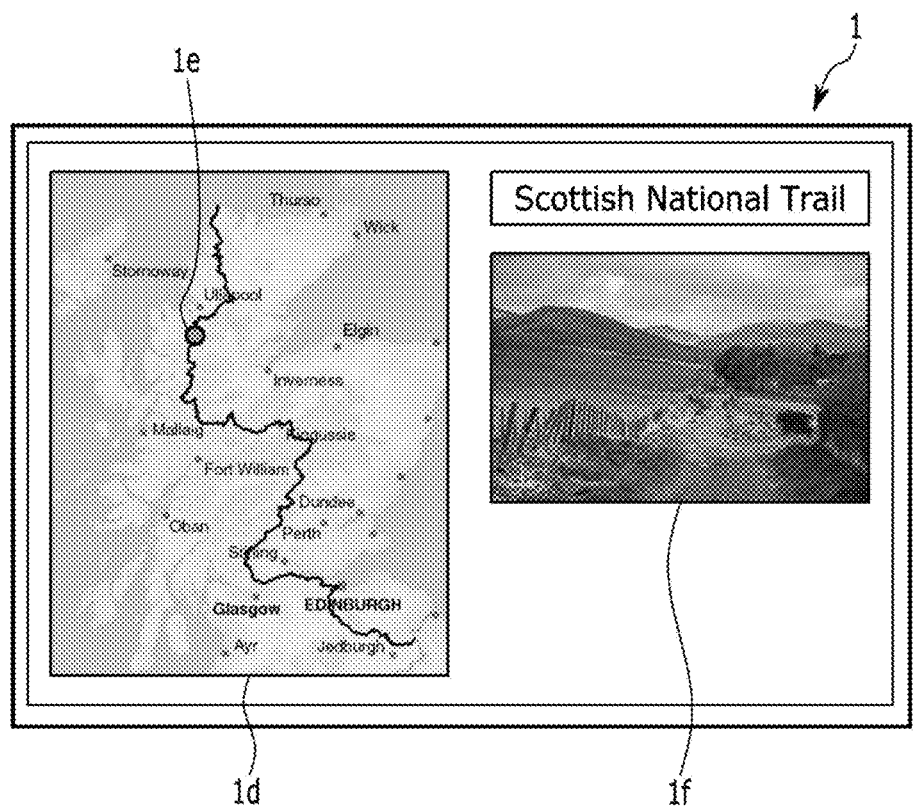
FIG. 4 is an exemplary diagram showing an exercise start location selection screen displayed in a terminal of the system for providing a virtual exercise place according to an implementation of the disclosed technology.

FIG. 3 is an exemplary diagram showing a virtual exercise place selection screen displayed in a terminal of the system for providing a virtual exercise place according to an implementation of the disclosed technology. FIG. 4 is an exemplary diagram showing an exercise start location selection screen displayed in a terminal of the system for providing a virtual exercise place according to an implementation of the disclosed technology. The disclosed technology is not limited to the illustrated configuration.

A first user may access the image information database 110 through his or her own first terminal 1, may check a virtual exercise place list 1a (S110), and may select a virtual exercise place where the first user wants to take exercise. In order to help the selection of the first user, the first terminal 1 may receive a photo 1b and information 1c for the virtual exercise place written in the virtual exercise place list 1a from the image information database 110 and may display the received photo and information.

The virtual exercise place may include all of worldwide roads on which exercise can be taken. For example, in Korea, the virtual exercise place may include Cheonggye creek Night Walk, Way to Mount Seorak Towangseong Falls, DMZ Punch Bowl Dulle-gil Trail (Meonmejjaegil), Namhansanseong Dulle-gil Trail 5 Course (Seonggwak-gil), and so on.

The information 1c about the virtual exercise place may include information (history, a related accident, length, difficulty, etc.) about the corresponding exercise place. In the information 1c about the virtual exercise place, an input window in which a user's experiences can be posted may be configured, and experiences posted by users may be displayed. The first user may post his or her own experiences on the input window configured in the information 1c about the virtual exercise place or may read experiences posted by other users. Such posting may be shared through other SNS programs (for example, Facebook, Instagram, KakaoStory and Pod cast). Contents and posting described in the information 1c about the virtual exercise place may be shared together.

When the first user selects the virtual exercise place, a screen 1d on which an exercise start location can be selected is displayed in the first terminal 1. Courses capable of exercise in the virtual exercise place are displayed, and the user may select an exercise start location 1e. When the user selects the exercise start location 1e, a scene 1f seen at the front from the exercise start location 1e is displayed. The scene 1f may be changed depending on the exercise direction.

The image data controller 120 receives from the first terminal 1 the virtual exercise place and the exercise start location (S120), and may select location-based image data related to the virtual exercise place (hereinafter referred to as "exercise place image data") in the image information database 110 and transmit the exercise place image data to the first terminal 1 (S130). For example, the image data controller 120 may select exercise place image data corresponding to the GPS coordinates of the virtual exercise place selected by the first user, and may transmit the selected exercise place image data to the first terminal 1. The image 1*f* of the exercise place image data may be displayed in the first terminal. In FIG. 4, the image 1*f* of the exercise place image data has been illustrated as a small screen, but may be changed into a mode in which the exercise place image data is displayed on a full screen.

The image data controller 120 may receive exercise distance information calculated by the first fitness equipment 11 from the first terminal 1 connected to the first fitness equipment 11 (S140), and may display in the first terminal 1 the image of the exercise place image data corresponding to the location moved by an exercise distance from the exercise start location (hereinafter referred to as a "virtual current location")(S150). For example, the image data controller 120 may obtain exercise distance information through a known distance calculator mounted on a treadmill or cycling equipment and the first terminal 1 connected thereto using a wired/wireless method. The image data controller 120 may select from the image information database 110 the exercise place image data corresponding to the GPS coordinates of the virtual current location into which exercise distance information has been incorporated, and may transmit the selected exercise place image data to the first terminal 1. The image 1*f* of the exercise place image data for the virtual current location may be displayed in the first terminal 1.

As described above, when the first user takes exercise in the first fitness equipment, the exercise place image data continues to be updated in real time. As if the first user enters the virtual exercise place and takes exercise, a scene displayed to the first user in the first terminal 1 is changed in accordance with an exercise distance.

The slope activation unit 150 may apply a load, corresponding to gradient data corresponding to a virtual current location, to the first fitness equipment 11 or may apply a gradient, corresponding to gradient data corresponding to a virtual current location, to the first fitness equipment 11 through the first terminal 1 connected to the load control device of the first fitness equipment 11 in a wired/wireless way. For example, when a slope increases, the slope activation unit may increase a load of cycling equipment or increase the foothold slope of a treadmill, thereby making exercise of the first user more difficult.

Figure 5:
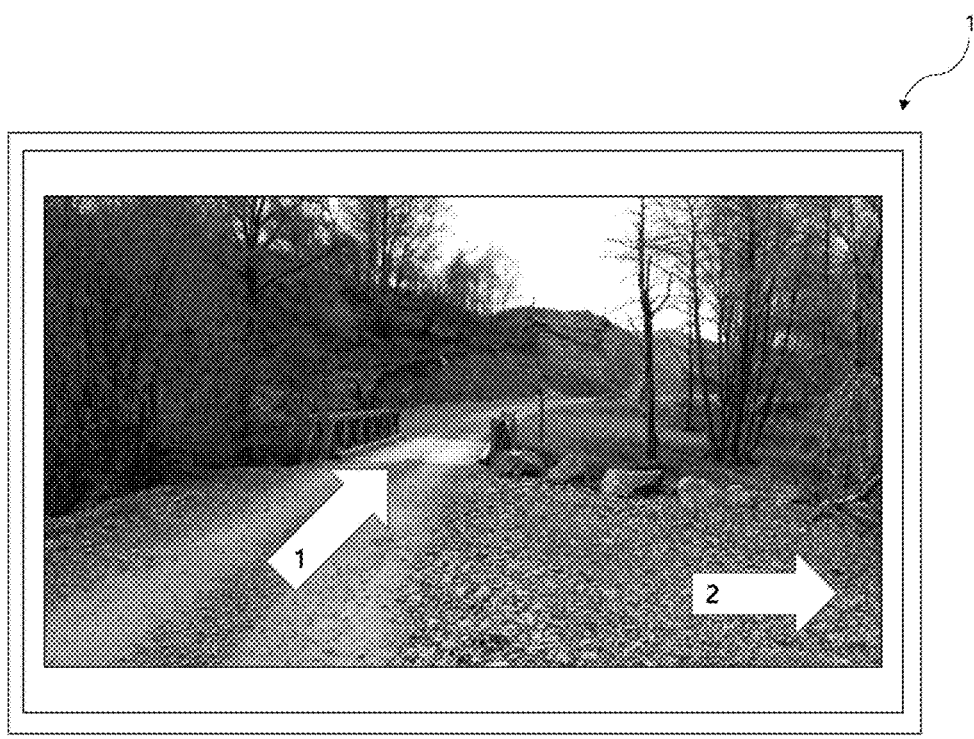
FIG. 5 is an exemplary diagram showing a course change screen displayed in a terminal of the system for providing a virtual exercise place according to an implementation of the disclosed technology.

FIG. 5 is an exemplary diagram showing a course change screen displayed in a terminal of the system for providing a virtual exercise place according to an implementation of the disclosed technology.

While the first user takes exercise according to a course first determined in the first fitness equipment, the first user may change the course into a new course. The image data controller 120 may transmit a course selection message, including information indicating that the course may be changed and courses that may be selected, to the first terminal 1 when the virtual current location reaches a course selection point (for example, a forked road) of the exercise place image data. The first user may select a desired course (for example, No. 1 arrow or No. 2 arrow in FIG. 5) through the first terminal 1. The image data controller 120 may display in the first terminal 1 the image of the exercise place image data corresponding to the course selected by the first terminal 1.

Figure 6:
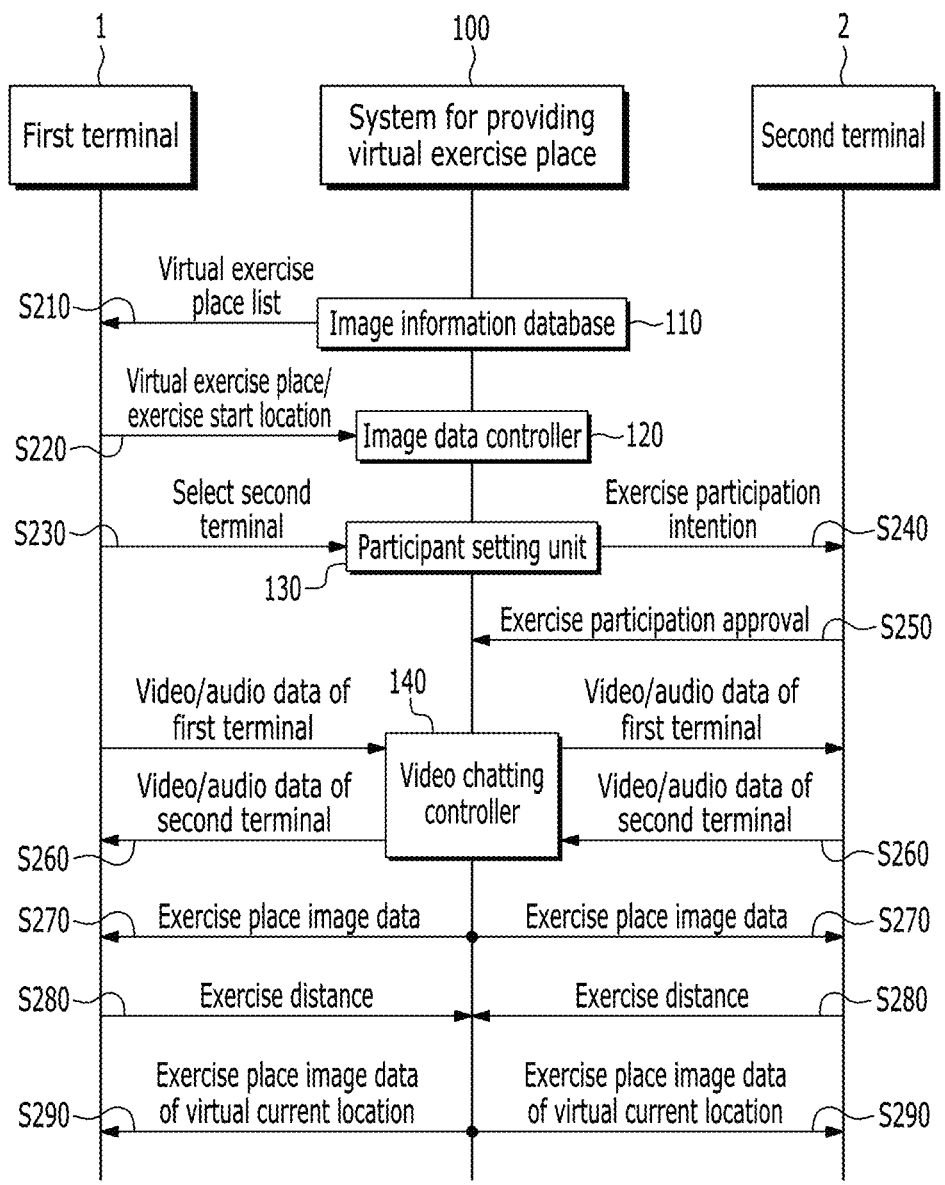
FIG. 6 is an exemplary flowchart showing a method of providing a virtual exercise place applied when a plurality of users uses the system for providing a virtual exercise place according to an implementation of the disclosed technology.

FIG. 6 is an exemplary flowchart showing a method of providing a virtual exercise place applied when a plurality of users uses the system for providing a virtual exercise place according to an implementation of the disclosed technology.

Figure 7:
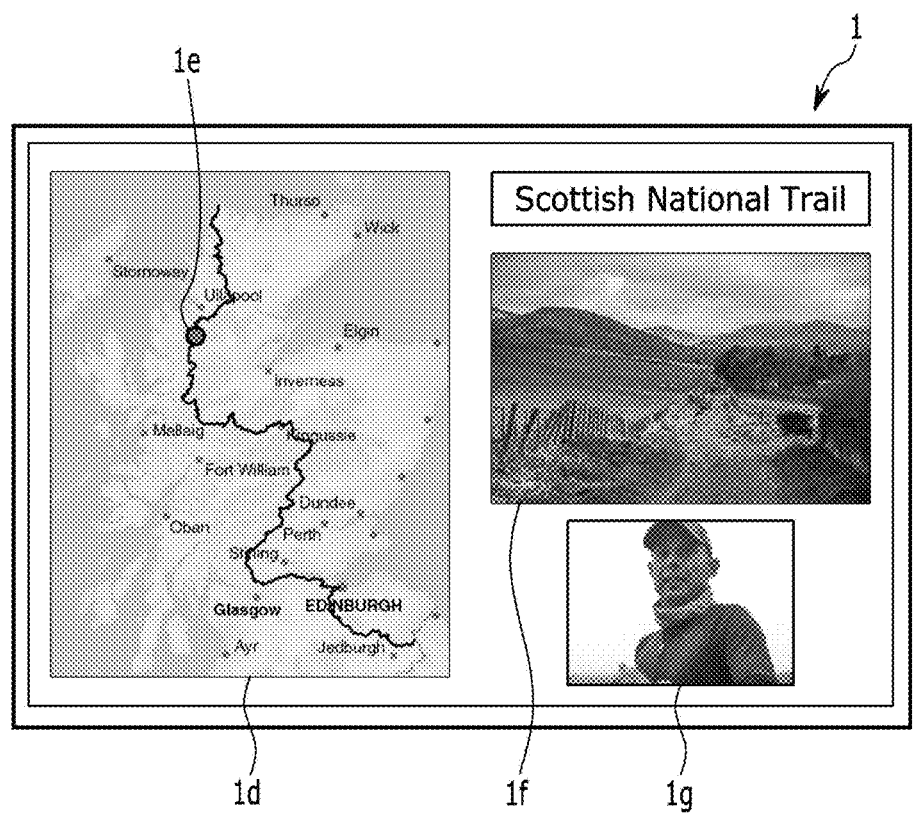
FIG. 7 is an exemplary diagram showing an exercise start location selection screen displayed in a terminal if a plurality of users uses the system for providing a virtual exercise place according to an implementation of the disclosed technology.

FIG. 7 is an exemplary diagram showing an exercise start location selection screen displayed in a terminal if a plurality of users uses the system for providing a virtual exercise place according to an implementation of the disclosed technology.

A first user may access the image information database 110 through his or her own first terminal 1, may check the virtual exercise place list 1*a* (S210), and may select a virtual exercise place where the first user wants to take exercise. As shown in FIG. 3, in order to help the selection of the first user, the first terminal 1 may receive the photo 1*b* and information 1*c* for the virtual exercise place written in the virtual exercise place list 1*a* from the image information database 110, and may display the received photo 1*b* and information 1*c*.

The virtual exercise place may include all of worldwide roads on which exercise can be taken. For example, in Korea, the virtual exercise place may include Cheonggye creek Night Walk, Way to Mount Seorak Towangseong Falls, DMZ Punch Bowl Dulle-gil Trail (Meonmejjaegil), Namhansanseong Dulle-gil Trail 5 Course (Seonggwak-gil), and so on.

The information 1*c* about the virtual exercise place may include information (history, a related accident, length, difficulty, etc.) about the corresponding exercise place. In the information 1*c* about the virtual exercise place, an input window in which a user's experiences can be posted may be configured, and experiences posted by users may be displayed. The first user may post his or her own experiences on the input window configured in the information 1*c* about the virtual exercise place or may read experiences posted by other users. Such posting may be shared through other SNS programs (for example, Facebook, Instagram, KakaoStory and Pod cast). Contents and posting described in the information 1*c* about the virtual exercise place may be shared together.

When the first user selects the virtual exercise place, the screen 1*d* on which an exercise start location can be selected is displayed in the first terminal 1 as shown in FIG. 4. Courses on which exercise can be taken in the virtual exercise place are displayed. The user may select the exercise start location 1*e* (S220). When the user selects the exercise start location 1*e*, the front scene 1*f* seen from the exercise start location 1*e* is displayed.

The first user may select one or more partners with whom the first user can take exercise in the virtual exercise place. The first user may select a second user as a partner with whom the first user will take exercise through the first terminal 1. The first terminal 1 transmits a signal, providing notification that the second user has been selected as a partner with whom the first user will take exercise, to the participant setting unit 130 (S230). The second user may be a person who lives in a different country and may be a person who takes exercise in the same space. The participant setting unit 130 may transmit to the first terminal 1 a list of users who have accessed the system for providing a virtual exercise place so that the first user can easily select a partner with whom the first user will take exercise.

A signal asking an exercise participation intention may be transmitted from the participant setting unit 130 to the second terminal 2 of the second user (S240). The second user may transmit an exercise participation approval signal to the participant setting unit 130 (S250) or may transmit an exercise participation refusal signal to the participant setting unit 130 through the second terminal 2. When the participant setting unit 130 receives the exercise participation approval signal from the second terminal 2, an image 1g of the second user photographed by the second terminal 2 is displayed in the first terminal 1.

In FIGS. 1 and 4, the system 100 for providing a virtual exercise place has been illustrated as being connected to the two terminals 1 and 2, but this is only an example for convenience of description of the disclosed technology. Three or more terminals may be connected to the system 100 for providing a virtual exercise place. Accordingly, the system 100 for providing a virtual exercise place may be used in group exercise of a group, such as a club, and may use a method in which celebrities who have approved exercise participation from among the celebrities of internal and external sports, medicine, entertainment, politics, culture and art fields participate in exercise along with multiple users. Furthermore, the participant setting unit 130 may include a virtual character (famous comic character, character having an image of himself or herself or celebrity, a virtual trainer character, etc.) in a list of partners with whom the first user will take exercise, and may provide the list to the first terminal 1. Such methods can greatly enhance users' interest and a degree of participation. The video chatting controller 140 may receive from the first terminal 1 video data, including an image of the first user photographed by the camera of the first terminal 1, and audio data, including the voice of the first user recorded by the microphone of the first terminal 1, and may receive from the second terminal 2 video data, including an image of the second user photographed by the camera of the second terminal 2, and audio data, including the voice of the second user recorded by the microphone of the second terminal 2. The video chatting controller 140 may transmit the video data and audio data of the first user to the second terminal 2, and may transmit the video data and audio data of the second user to the first terminal 1 (S260).

If a virtual character has been selected as a partner with whom the first user will take exercise, the video chatting controller 140 may transmit the video data and audio data of the selected character to the first terminal 1. In this case, the virtual character may talk and behave according to artificial intelligence.

Furthermore, the video chatting controller 140 may transmit background music (song, pop song, classical music, etc.) to the terminals 1 and 2 so that the users can take exercise along with the background music.

After the virtual exercise place and the exercise start location are received from the first terminal 1, the image data controller 120 may select exercise place image data from the image information database 110 and transmit it to the first terminal 1 and the second terminal 2 (S270). For example, the image data controller 120 may select exercise place image data corresponding to the GPS coordinates of the virtual exercise place selected by the first user, and may transmit the selected exercise place image data to the first terminal 1 and the second terminal 2. The image 1f of the exercise place image data may be displayed in the first terminal 1 and the second terminal 2. In FIG. 7, each of the image 1f of the exercise place image data and the image 1g of the second user has been illustrated as a small screen, but may be changed into a mode in which the image of the exercise place image data and the image of the second user are displayed on a full screen.

The image data controller 120 may receive exercise distance information calculated by the first fitness equipment 11 (S280), and may display the image of the exercise place image data corresponding to a virtual current location to the first terminal 1 and the second terminal 2 (S290). For example, the image data controller 120 may obtain the exercise distance information through a known distance calculator mounted on a treadmill or cycling equipment and the first terminal 1 and the second terminal 2 connected thereto using a wired/wireless method. The image data controller 120 may select from the image information database 110 exercise place image data corresponding to the GPS coordinates of a virtual current location into which the exercise distance information has been incorporated, and may transmit the selected exercise place image data to the first terminal 1 and the second terminal 2. The image 1f of the exercise place image data for the virtual current location may be displayed in the first terminal 1 and the second terminal 2.

In this way, as the first user and the second user take exercise in the first fitness equipment and the second fitness equipment, respectively, the image of the exercise place image data continues to change. As if the first user and the second user enter the virtual exercise place and take exercise together, scenes displayed to the first user and the second user through the first terminal 1 and the second terminal 2 are changed in accordance with an exercise distance.

There may be a difference between the virtual current location of the first user and the virtual current location of the second user due to a difference in the exercise speed between the first user and the second user. In this case, different exercise place image data may be displayed in the first terminal 1 and the second terminal 2.

The slope activation unit 150 may apply to the first fitness equipment 11 and the second fitness equipment 12 a load, corresponding to gradient data corresponding to a virtual current location, or apply a gradient, corresponding to the gradient data corresponding to the virtual current location, to the first fitness equipment 11 and the second fitness equipment 12 through the first terminal 1 connected to the load control devices of the first fitness equipment 11 and the second fitness equipment 12 in a wired/wireless manner. For example, when the slope increases, the slope activation unit 150 may increase a load of cycling equipment or increase the foothold slope of a treadmill, thereby being capable of making further difficult exercise of the first user and the second user.

Meanwhile, while the first user and the second user take exercise on a course first determined in the first terminal 1, they may change the course into a new course. When a virtual current location reaches a course selection point (for example, a forked road) of exercise place image data, the image data controller 120 may transmit to the first terminal 1 and/or the second terminal 2 a course selection message, including information indicating that the course may be changed and courses that may be selected. Any one of the first user and the second user may select a desired course (for example, No. 1 arrow or No. 2 arrow of FIG. 5) through the first terminal 1 or the second terminal 2. Exercise place image data corresponding to a course first selected by any one of the first terminal 1 and the second terminal 2 may be displayed in the first terminal 1 and the second terminal 2. Accordingly, a user who has first reached a forked road has priority to determine a course, and thus there is an effect in that an interest in exercise can be increased through a competition.

Furthermore, when the virtual current location of another user who accesses the system 100 and takes exercise is close to the virtual current location of the first user or the second user, the video chatting controller 140 may display an image of another user in the first terminal 1 and the second terminal 2 and output a voice of another user through the first terminal 1 and the second terminal 2, whereby the video chatting controller 140 can notify the first user and the second user that another user takes exercise in the space where the first user and the second user take exercise. Accordingly, exchange between users can become active, and users can have an interest in virtual moving exercise so that they are further immersed in the virtual exercise space. Users who have met together in the virtual exercise space as described above may move together by transmitting a joint signal through the participant setting unit 130. In this case, the same exercise place image data may be displayed in the terminals of the users.

The system 100 for providing a virtual exercise place may provide an event to users who take exercise together. The image data controller 120 provides a first arrival event for a specific section (a course deviated from the first course is preferred) to users who take exercise together so that the users autonomously select a course at each forked road, run at full speed, and first reach a target point. When the event starts, independent exercise place image data is displayed in the terminals of the users. A reward, such as that the period of use of the system 100 is extended, may be provided to a user who has first reached the target point. When all the users reach the target point, the image data controller 120 may transmit the same exercise place image data to the terminals of the users like in the beginning, so the users can take exercise together.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve described results. Moreover, the separation of various system components in the embodiments described in this patent document should not be understood as requiring such separation in all embodiments. Only a few implementations and examples are described. Other implementations, enhancements and variations can be made based on what is described and illustrated in this patent document.

DESCRIPTION OF REFERENCE NUMERALS

110: image information database
120: image data controller
130: participant setting unit
140: video chatting controller
150: slope activation unit

The invention claimed is:

1. A system for providing a virtual exercise place, which is connected to terminals comprising a camera and a microphone and fitness equipment capable of calculating exercise distances and transmits an image of the virtual exercise place to the terminals, the system comprising:
   an image information database in which location-based image data related to the virtual exercise place is stored;
   a participant setting unit transmitting to a second terminal a signal asking an exercise participation intention received from a first terminal and receiving an exercise participation approval signal from the second terminal;
   an image data controller selecting from the image information database location-based image data related to the virtual exercise place received from the first terminal and transmitting the selected location-based image data to the first terminal and the second terminal, displaying in the first terminal and the second terminal an image corresponding to an exercise start location received from the first terminal or second terminal, receiving a first exercise distance calculated by a first fitness equipment and a second exercise distance calculated by a second fitness equipment, and displaying in the first terminal an image corresponding to a first virtual current location, the first virtual current location being the location moved by the first exercise distance from the exercise start location, and displaying in the second terminal an image corresponding to a second virtual current location, the second virtual current location being the location moved by the second exercise distance from the exercise start location; and
   a video chatting controller receiving from the first terminal and the second terminal video data of a first user using the first terminal and a second user using the second terminal, photographed by the camera of the first terminal and the second terminal, and audio data comprising voices of the first user and the second user, recorded by the microphones of the first terminal and the second terminal, transmitting the video data and the audio data of the first user to the second terminal, and transmitting the video data and audio data of the second user to the first terminal,
   wherein when a virtual current location of a third terminal, the third terminal having a different exercise start location than the first terminal, enters a proximity of the virtual current location of the first terminal or the second terminal, the video chatting controller receives from the third terminal video data of a third user using the third terminal, photographed by the camera of the third terminal, and audio data comprising voices of the third user, recorded by the microphone of the third terminal, transmits the video data and audio data of the third user to the first terminal and the second terminal, and transmits the video data and audio data of the first user and the second user to the third terminal, and
   wherein when the third terminal transmits a joint signal asking exercise participation intention to the first terminal or the second terminal through the participant setting unit, and the participant setting unit receives a third terminal exercise participation approval signal from the first terminal or the second terminal, the video chatting controller displays in the third terminal an image corresponding to the virtual current location of the first terminal and the second terminal in response.

2. The system of claim 1, wherein:
   the image information database further comprises historical information related to the virtual exercise place; and the image data controller selects from the image information database the historical information related to the virtual exercise place, transmits the selected historical information to the first terminal and the second terminal, and displays in the first terminal and the second terminal the historical information.

3. The system of claim 1, wherein:

the image information database further comprises user experience information related to the virtual exercise place; and the image data controller selects from the image information database the user experience information related to the virtual exercise place, transmits the selected user experience information to the first terminal and the second terminal, and displays in the first terminal and the second terminal the user experience information.

4. The system of claim 1, wherein:

the image information database further comprises course selection information corresponding to a virtual location of the virtual exercise place;

the image data controller selects from the image information database the course selection information corresponding to the virtual location of the virtual exercise place when the first virtual current location or the second virtual current location approaches a course selection point within the virtual location, transmits the selected course selection information to the first terminal and the second terminal, and displays in the first terminal and the second terminal the course selection information; and the first terminal or the second terminal transmits a user course selection, made by the first or the second user in response to the displayed course selection information, to the image data controller to change a virtual course of the first and second user.

5. The system of claim 1, wherein:

the participant setting unit contains audio data and video data of a virtual character; and the video chatting controller transmits the virtual character audio data and video data to the first terminal in response to a selection of the virtual character by the first user.

* * * * *